United States Patent [19]

Hassell

[11] 4,334,530

[45] Jun. 15, 1982

[54] INDICIA-BEARING ADHESIVE BANDAGES

[76] Inventor: Donald S. Hassell, 37 Westdale Rd., Holbrook, Mass. 02343

[21] Appl. No.: 186,759

[22] Filed: Sep. 12, 1980

[51] Int. Cl.³ .............................................. A61L 15/00
[52] U.S. Cl. ................................................... 128/156
[58] Field of Search ................................ 128/155–156

[56] References Cited

U.S. PATENT DOCUMENTS

| 2,905,174 | 9/1959 | Smith | 128/156 |
| 3,425,412 | 2/1969 | Pope | 128/156 |
| 3,695,258 | 10/1972 | Castle | 128/156 |

Primary Examiner—C. Fred Rosenbaum

[57] ABSTRACT

Novel adhesive bandages having indicia or markings indicating the direction of removal without reopening or otherwise impairing healing of the wound covered thereby.

5 Claims, 10 Drawing Figures

INDICIA-BEARING ADHESIVE BANDAGES

BACKGROUND OF THE INVENTION

This invention is directed to adhesive bandages of the type generally used for first aid and surgical dressings and which are usually referred to as "strip" type bandages wherein an absorbent protective pad or gauze dressing is carried by an adhesive-coated flexible backing. Such adhesive bandages are so well known and staple items in a first aid kit or medicine cabinet that they need not be discussed in great detail.

While such bandages are used for a multitude of skin irritations and wounds, the present invention is in particular directed to their use as a dressing for flap-like or "U-shaped" wounds and the invention will accordingly be discussed hereinafter with reference to such wounds.

With flap wounds, care must be taken when removing or changing the bandage so as not to reopen or otherwise harm the wound and thereby set back the healing process. While this may not generally be a serious problem with physicians, nurses and other medically oriented users who are of course highly skilled in such procedures, it presents a very real problem to the ordinary layman attending to his own first aid needs.

In a sense, it can be said there is a right way and a wrong way to remove an adhesive bandage from a flap wound. If the tape is peeled back in the direction of the flap wound, the wound is very likely to be reopened, much as one peels a banana. This would particularly be true if there is even slight adherance or adhesion of the healing skin to the protective pad, causing it to be peeled back away from the wound as the bandage is itself peeled away. On the other hand, if the adhesive is peeled back in the opposite direction away from the direction of the flap wound, this danger will be obviated. The problem however is remembering the direction of the flap wound, i.e. whether the adhesive bandage should be peeled away from right-to-left or from left-to-right. This of course presupposes that the user is even knowledgable enough to know and understand that there is in fact a right way and a wrong way to remove a dressing from such wounds.

SUMMARY OF THE INVENTION

In accordance with the present invention, this inherent problem is obviated in a simple, efficient and elegant manner by providing markings or indicia on the adhesive bandage indicating the direction of removal. Such indicia, which may be provided by etching or scoring the bandage, printing or in any other per se known manner for applying indicia to a surface, may be in any form which will be understood by the user to indicate the direction of removal. The selection of the particular indicia to accomplish the objectives to which this invention is directed is varied and illustrative forms and embodiments will be detailed hereinafter.

DETAILED DESCRIPTION OF THE INVENTION

As was mentioned previously, the present invention is directed to adhesive bandages of the known type and, in particular, to provide means associated with such bandages to facilitate proper removal, especially from flap-like wounds.

The nature and objects of the invention will be more fully understood by reference to the following detailed disclosure taken in conjunction with the accompanying drawings.

Figure 3:
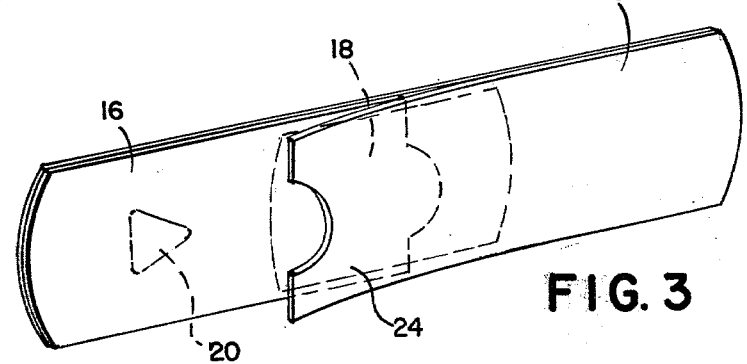
FIG. 3 is a rear view of the bandage of FIG. 2.

The problem to which the invention is primarily directed can best be explained by reference to FIG. 1. As illustrated therein, an adhesive bandage 10 of per se known configuration is shown to have been applied to a flap wound 12 of a finger 14. Bandage 10 comprises an adhesive-coated strip or strips 16 on which an absorbent pad 18 intended to be placed over the wound is medially disposed between transverse edges 22a, 22b of strip 16. In the usual form, strip 16 comprises a flexible backing coated on one side with a pressure-sensitive adhesive. Absorbent pad 18 is typically made of sterile gauze or the like and is carried on the adhesive-faced side, usually medially positioned between the transverse edges as shown. As is shown in FIG. 3, a pair of removable release sheets 24 are generally provided to protect the adhesive face and the absorbent pad, which release sheets are of course removed prior to applying the bandage.

When positioned on the wound, the bandage is of course removable by peeling away from either direction, e.g. by peeling away tape 16 from left to right or from right to left.

Figure 1:
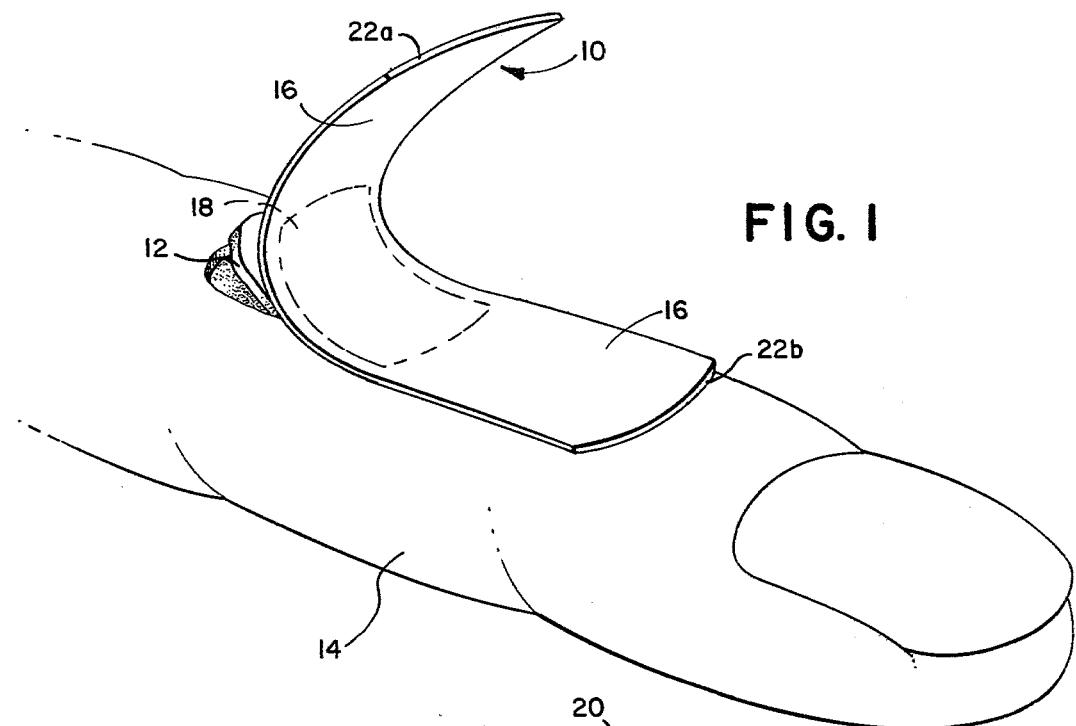
FIG. 1 is a perspective view of a conventional adhesive bandage of the type contemplated herein illustrating the problem to which the invention is directed.

As shown in FIG. 1, if bandage 10 is peeled first from the flap wound, the healing new skin would tend to be peeled back also in a hinge-like action, thereby reopening the wound. This would be particularly true if the absorbent pad 18 covering the wound was not appropriately lubricated and/or the healing tissue had any tendency towards adherance to the dressing. The reopening of the wound in this manner is shown in FIG. 1.

It can be said conversely that had the adhesive bandage been peeled away in the reverse direction starting first with the healthy skin covered by dressing, e.g. from right to left as one views FIG. 1, the flap wound would not be harmed. The problem is to remember the direction of the flap wound in order to know in which direction to peel away the bandage when changing the dressing. This problem constitutes the primary task of this invention.

In accordance with the invention, this problem is obviated by applying indicia on the surface of the bandage opposite the dressing, i.e. the surface of the bandage which would by visible after the bandage is applied. This indicia is preferably disposed intermediate the pad 18 and one of the transverse edges 22a or 22b of strip 16.

Figure 2:
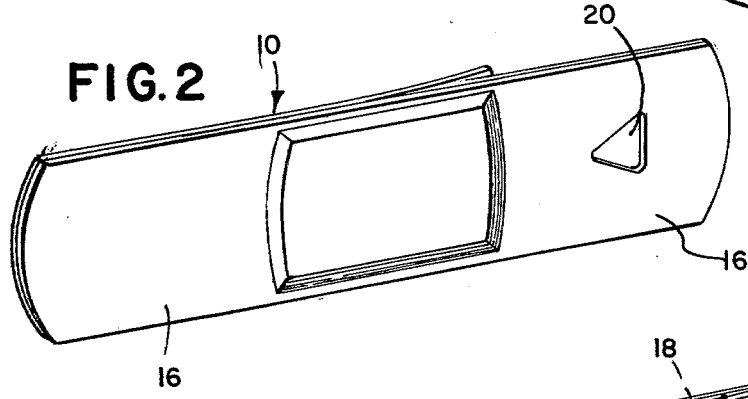
FIG. 2 is a perspective view of a novel adhesive bandage of this invention.

As shown in FIG. 2, indicia 20 may be in the general form of an arrow which, in accordance with the general instructions which would be supplied for usage, should point in the proper direction for removal. Thus, if the novel adhesive bandage of this invention had been used in the manner illustrated in FIG. 1, the bandage would be positioned with the arrow pointing to the left, as one views the Figure, thereby indicating the bandage should be peeled away from the right to the left or in the reverse direction from that shown in FIG. 1.

Figure 4:
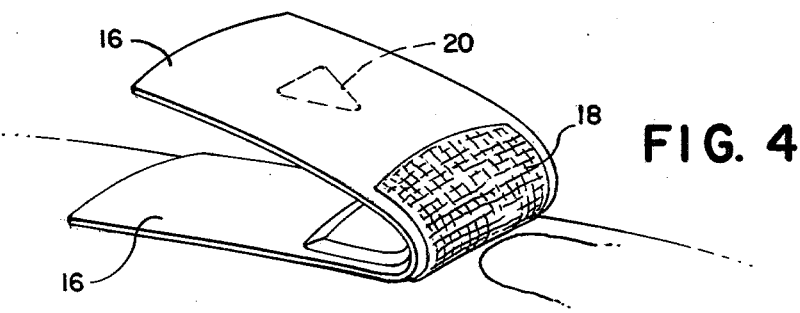
FIG. 4 is a perspective view of the bandage of FIGS. 2, 3 partially removed or peeled back to illustrate the practice of the invention.
Figure 5:
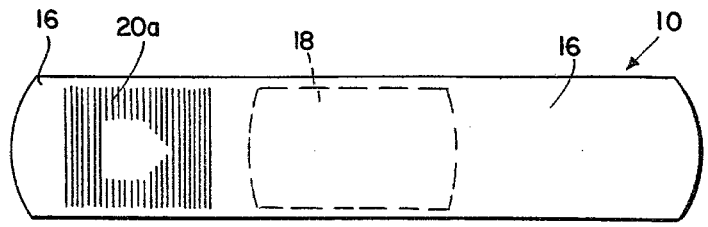
FIGS. 5-10 are plan views illustrating alternate forms of embodiments of the invention.
Figure 6:
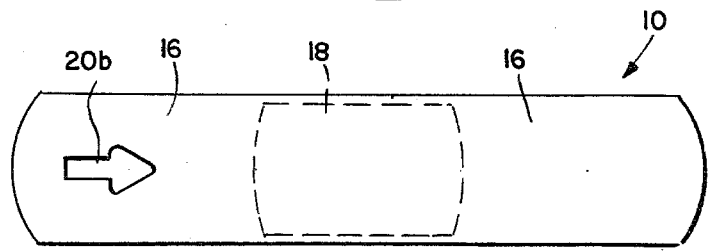
Figure 7:
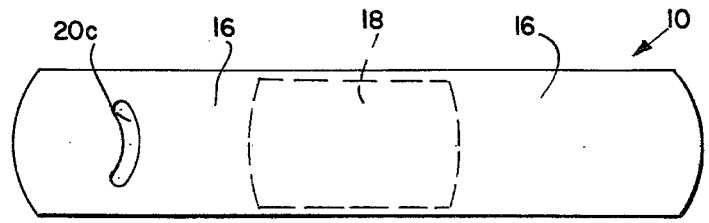
Figure 8:
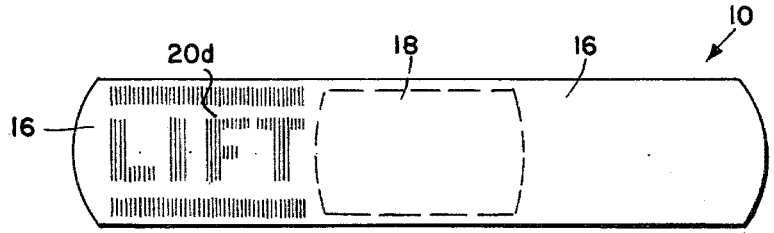
Figure 9:
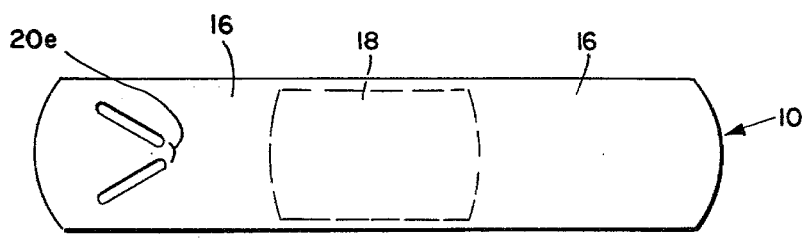
Figure 10:
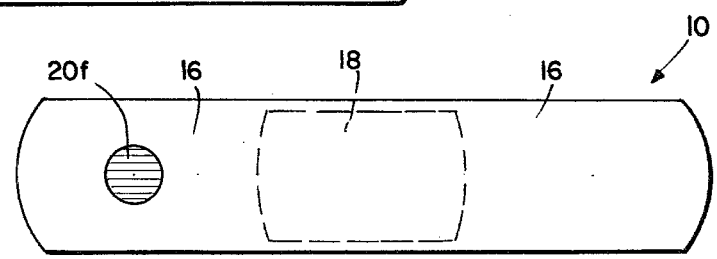

Removal of the bandage in the proper manner with the indicia-bearing bandages of this invention is shown in FIG. 4.

The particular configuration or design of the indicia can be in various forms, depending upon the individual whim of the practitioner. Many variations will of course by readily suggested in the light of the foregoing description. Suitable illustrative variations 20a, 20b, 20c, 20d, 20e and 20f are shown in FIGS. 5-10, respectively.

While the precise design or configuration selected should clearly and unequivocally show the direction of intended or proper removal, it will be appreciated that from the cost of manufacture only, the design should ideally also be relatively simple.

The indicia may be applied to the bandage in various ways. It could be applied by lamination of a flexible sheet material, e.g. with heat or pressure sensitive adhesives, to the non-adhesive side of strip 16. It could also be applied by carving, engraving or etching into the surface, or by means of suitable inks, dyes, or pigments which should preferably be relatively fast, water-insoluble and non-toxic. Such inks or dyes may be applied, for example, by gravure or any of the other per se known printing techniques. Other modes of application will also be readily suggested and are accordingly within the scope of this invention. Further by way of illustration only, one simple and efficient way is by engraving with a sharp or pointed instrument.

As mentioned, the adhesive bandages to which this invention is directed are per se known and of common usage in the home. The essence of the invention is the provision of the described simple, elegant and efficient means for facilitating removal from flap wounds and the like.

Since certain changes may be made in the above article without departing from the scope of the invention herein involved, it is intended that all matter contained in the above description shall be interpreted as illustrative and not in a limiting sense.

I claim:

1. In an adhesive bandage comprising a flexible backing, a pressure-sensitive adhesive on one side of said backing, an absorbent pad carried by said backing on said adhesive-faced side, said absorbent pad being positioned intermediate transverse edges of said backing;

the improvement wherein the other non-adhesive side of said backing is provided with markings indicating which transverse edge of said backing should be removed first when removing said bandage from a wound.

2. An adhesive bandage as defined in claim 1 wherein said markings are provided on said other side between said absorbent pad and one of the transverse edges of said backing.

3. An adhesive bandage as defined in claim 1 wherein said markings are in the shape of an arrow.

4. An adhesive bandage as defined in claim 1 wherein said markings are applied by laminating a flexible sheet material containing said markings to said other side of said backing.

5. An adhesive bandage as defined in claim 1 wherein said markings are applied by cutting said other side of said backing.

* * * * *